(12) United States Patent
Yanagawa et al.

(10) Patent No.: US 11,768,155 B2
(45) Date of Patent: Sep. 26, 2023

(54) DETECTION DEVICE AND DETECTION METHOD

(71) Applicant: Panasonic Intellectual Property Management Co., Ltd., Osaka (JP)

(72) Inventors: Hiroto Yanagawa, Osaka (JP); Masahiko Shioi, Osaka (JP); Kazuaki Nishio, Osaka (JP); Emina Ikeuchi, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 696 days.

(21) Appl. No.: 16/747,021

(22) Filed: Jan. 20, 2020

(65) Prior Publication Data

US 2020/0166455 A1    May 28, 2020

Related U.S. Application Data

(63) Continuation of application No. PCT/JP2018/034425, filed on Sep. 18, 2018.

(30) Foreign Application Priority Data

Sep. 21, 2017  (JP) ................. 2017-181836

(51) Int. Cl.
    *G01N 21/64*   (2006.01)
    *G01N 33/543*  (2006.01)
    *G01N 33/68*   (2006.01)

(52) U.S. Cl.
    CPC ..... *G01N 21/648* (2013.01); *G01N 33/54373* (2013.01); *G01N 33/6857* (2013.01); *G01N 2021/6441* (2013.01)

(58) Field of Classification Search
    CPC .......... G01N 21/648; G01N 33/54373; G01N 33/6857; G01N 2021/6441; G01N 21/553;

(Continued)

(56) References Cited

U.S. PATENT DOCUMENTS 9,868,778 B2    1/2018  Muraoka
2010/0041065 A1  2/2010  Horii et al.
2017/0030833 A1* 2/2017  Nakamura ......... G01N 21/6428

FOREIGN PATENT DOCUMENTS

JP    2010-043934    2/2010
JP    2011-158369    8/2011
(Continued)

OTHER PUBLICATIONS

Keiko Tawa, Mitsuo Umetsu, Hikaru Nakazawa, Takamitsu Hattori, and Izumi Kumagai. ACS Applied Materials & Interfaces 2013 5(17), 8628-8632. DOI: 10.1021/am402173y (Year: 2013).*

(Continued)

*Primary Examiner* — Christopher L Chin
(74) *Attorney, Agent, or Firm* — McDermott Will & Emery LLP

(57) ABSTRACT

The present disclosure provides a detection device capable of detecting a low concentration of an analyte with high sensitivity. The detection apparatus according to the present disclosure comprises a metal microstructure on which a first VHH antibody having a property of binding specifically to the analyte is immobilized and which generate surface plasmon by being irradiated with excitation light, an inlet through which a second VHH antibody and a sample that may contain an analyte are introduced, wherein the second VHH antibody has a property of binding specifically to the analyte and is labeled with a fluorescent substance, a light source for irradiating the metal microstructure to which the second VHH antibody and the sample have been introduced with the excitation light, and a detection unit for detecting the analyte on the basis of fluorescence generated from the fluorescent substance by the irradiation of the excitation light.

9 Claims, 8 Drawing Sheets

(58) Field of Classification Search
CPC .. G01N 21/554; G01N 21/6428; B82Y 15/00; B82Y 35/00; C07K 2317/569
USPC ............ 250/459.1; 356/320, 417; 422/82.08, 422/82.11; 436/172, 512, 514, 524, 525, 436/805; 435/7.92, 288.7, 808; 73/7.89; 530/866, 387.1, 389.1, 391.1; 977/918
See application file for complete search history.

(56) References Cited

FOREIGN PATENT DOCUMENTS

| JP | 2015-178993 | 10/2015 |
|---|---|---|
| JP | 2017-036258 | 2/2017 |
| WO | 2017/053516 | 3/2017 |

OTHER PUBLICATIONS

Tawa K, Nakayama T, Kintaka K. Optimal Structure of a Plasmonic Chip for Sensitive Bio-Detection with the Grating-Coupled Surface Plasmon-Field Enhanced Fluorescence (GC-SPF). Materials (Basel). Sep. 11, 2017;10(9):1063. doi: 10.3390/ma10091063. PMID: 28891989; PMCID: PMC5615717.) (Year: 2017).*

Huang et al ("Prostate-specific antigen immunosensing based on mixed self assembled monolayers, camel antibodies and colloidal gold enhanced sandwich assays", Biosensors and Bioelectronics, 21, 2005, 483-490) (Year: 2005).*

Hassanzadeh-Ghassabeh et al ("Nanobodies and their potential applications", Nanomedicine, vol. (8), Issue 6, Jun. 4, 2013, pp. 1013-1026) (Year: 2013).*

International Search Report of PCT application No. PCT/JP2018/034425 dated Dec. 25, 2018.

George P. Anderson et al., "Single domain antibody-quantum dot conjugates for ricin detection by both fluoroimmunoassay and surface plasmon resonance", Analytica Chimica Acta, May 14, 2013, vol. 786, pp. 132-138.

Joydeep Lahiri et al., "A Strategy for the Generation of Surfaces Presenting Ligands for Studies of Binding Based on an Active Ester as a Common Reactive Intermediate: A Surface Plasmon Resonance Study", Analytical Chemistry, vol. 71, No. 4, Feb. 15, 1999, 777-790, Published on Web on Jan. 8, 1999.

Dirk Saerens et al., "Engineering Camel Single-Domain Antibodies and Immobilization Chemistry for Human Prostate-Specific Antigen Sensing", Analytical Chemistry, vol. 77, No. 23, Dec. 1, 2005, 7547-7555, Published on Web on Oct. 25, 2005.

Xue Gong et al., "Specific determination of influenza H7N2 virus based on biotinylated single-domain antibody from a phage-displayed library", Analytical Biochemistry 500 (2016) 66-72, Oct. 9, 2015.

* cited by examiner

DETECTION DEVICE AND DETECTION METHOD

BACKGROUND

1. Technical Field

The present disclosure relates to a detection device and a detection method for detecting an analyte (for example, a virus) contained in a sample.

2. Description of the Related Art

Patent Literature 1 discloses a fluorescence method used as a publically well-known technique for detecting an analyte contained in a sample. In Patent Literature 1, first, an analyte to which an antibody labeled with a fluorescent substance (hereinafter, such an antibody is referred to as "labeled antibody") has been bound is bound on a sensor section via an antibody immobilized on the sensor section including a metal layer (hereinafter, such an antibody is referred to as "immobilized antibody"). Then, by irradiating the sensor section with excitation light, plasmon is excited in the metal layer to generate an optical electric field enhanced by the plasmon. The amount of fluorescence generated from the fluorescent substance of the labeled antibody in the enhanced optical electric field is measured to detect the amount of the analyte.

In Patent Literature 1, a fragmented antibody is used as the immobilized antibody. As a result, a distance between the fluorescent substance and the metal layer is made shorter, compared to a case of using an ordinary antibody, and an optical signal is allowed to be detected with high sensitivity by efficiently utilizing the enhanced optical electric field.

CITATION LIST

Patent Literature

Patent Literature 1: Japanese Patent Application Publication No. 2010-043934
Patent Literature 2: Japanese Patent Application Publication No. 2015-178993
Patent Literature 3: Japanese Patent Application Publication No. 2017-036258

SUMMARY

However, in the prior art using the above-described fragmented antibody, it is difficult to detect a low concentration of the analyte.

Thus, the present disclosure provides a detection device and a detection method capable of detecting a low concentration of an analyte with high sensitivity.

The detection device of the present disclosure comprises:
- a metal microstructure on which a first VHH antibody having a property of binding specifically to an analyte is immobilized; surface plasmon being generated by irradiating the metal microstructure with excitation light,
- an inlet through which a second VHH antibody and a sample that may contain an analyte are introduced, wherein the second VHH antibody has a property of binding specifically to the analyte and is labeled with a fluorescent substance;
- a light irradiation unit for irradiating the metal microstructure to which the second VHH antibody and the sample have been introduced with the excitation light; and
- a detection unit for detecting the analyte on the basis of fluorescence generated from the fluorescent substance by the irradiation of the excitation light.

Note that these inclusive or specific aspects can be realized by a system, a method, an integrated circuit, a computer program, or a recording medium such as a computer-readable CD-ROM and that these inclusive or specific aspects can be realized by any combination of a system, a method, an integrated circuit, a computer program and a recording medium.

According to the present disclosure, a low concentration of an analyte can be detected with high sensitivity.

Figure 1:
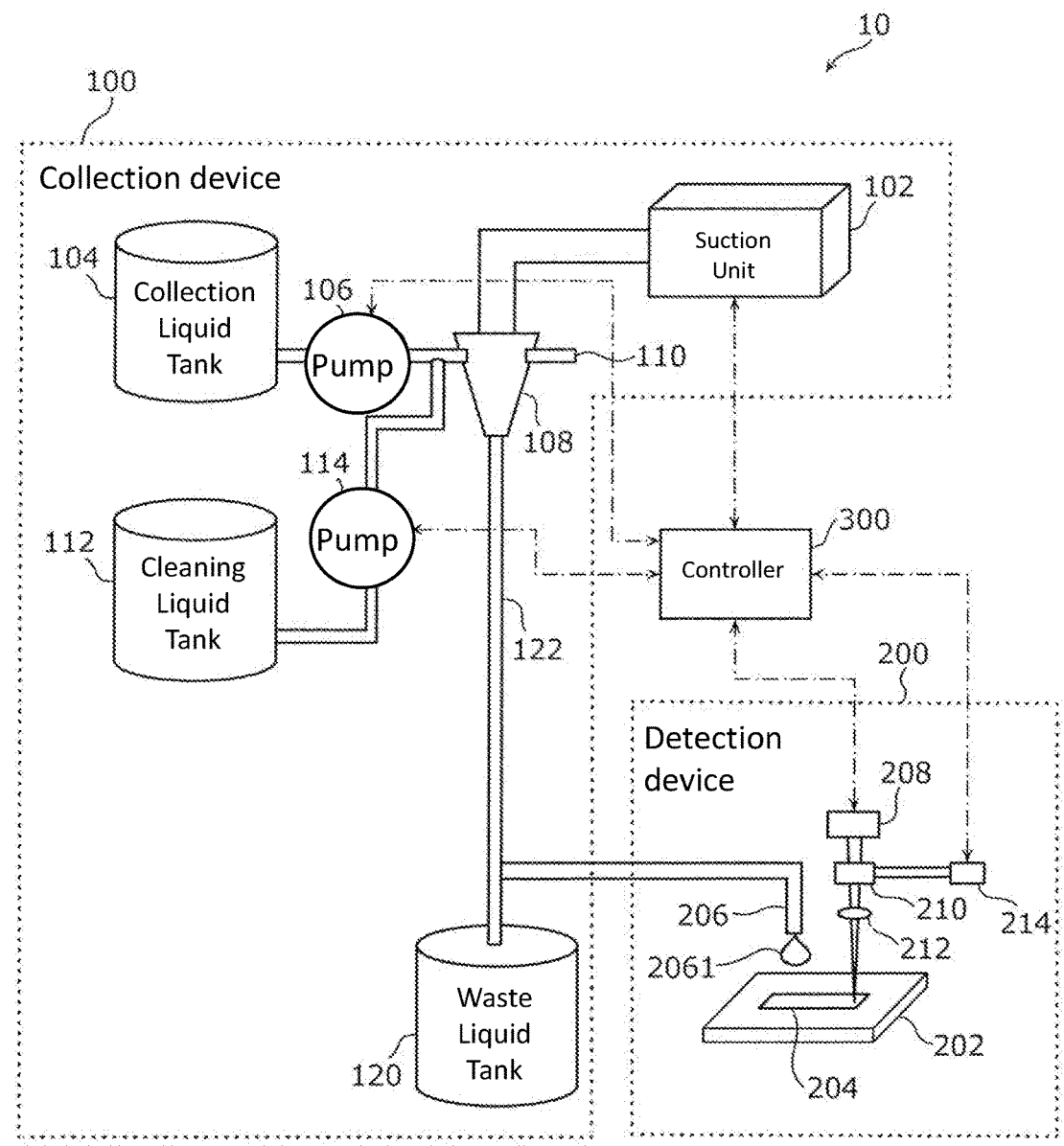
FIG. 1 is a schematic view of a detection system according to a first embodiment.
Figure 2:
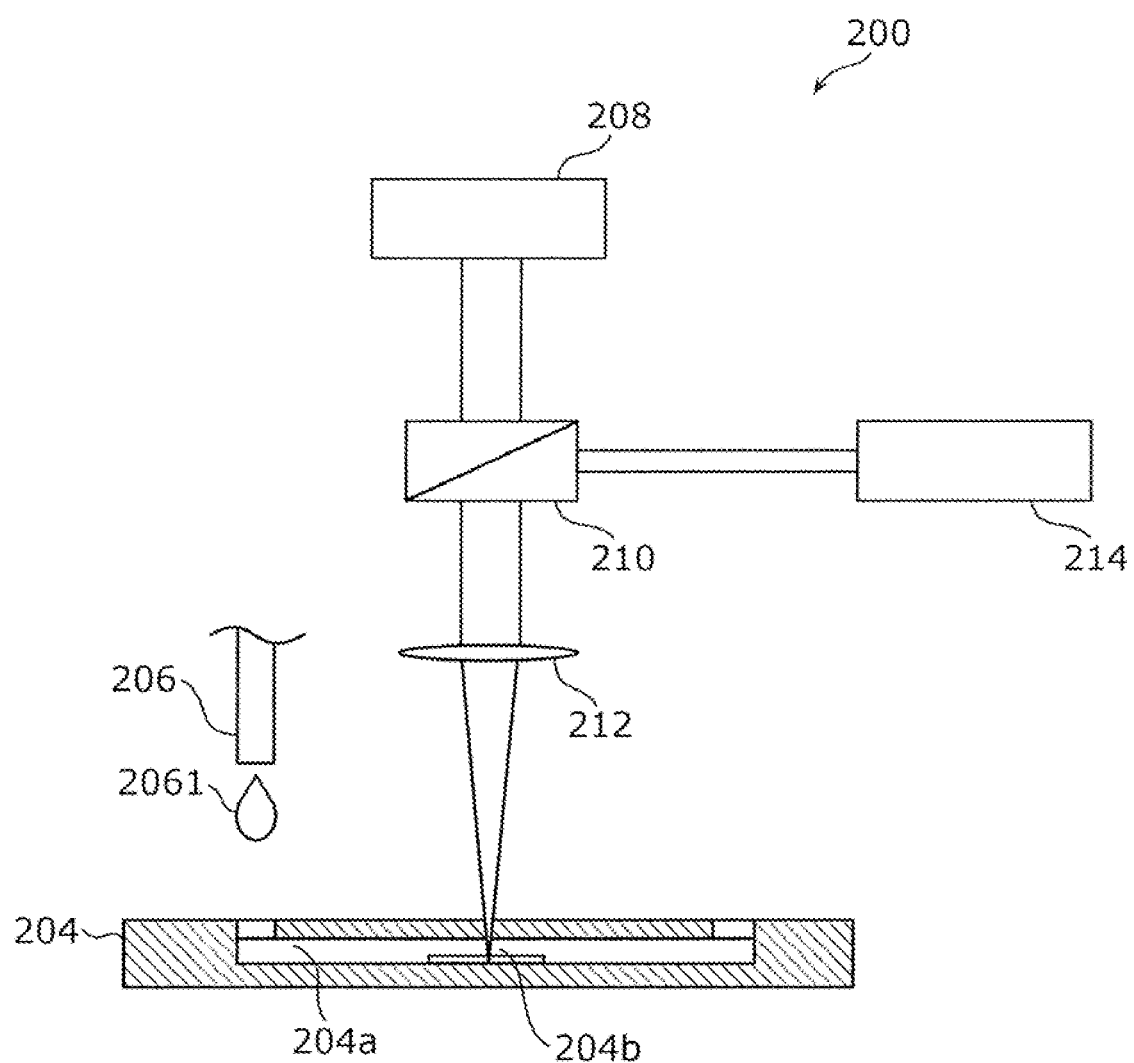
FIG. 2 is a schematic view of a detection device according to the first embodiment.

DETAILED DESCRIPTION (Findings that Establishes the Fundamentals of the Present Disclosure)

As described above, it is difficult to detect a low concentration of an analyte in the prior art using a fragmented antibody. The present inventors have found that the reason therefor is a decrease in an antigen capturing ability due to antibody fragmentation. Since the antigen capturing ability of the fragmented antibody is lower than those of normal antibodies, it is difficult for the immobilized antibody to bind to a low concentration of the analyte. This decreases detection sensitivity.

To solve the above problem, the detection device of the present disclosure comprises:
- a metal microstructure on which a first VHH antibody having a property of binding specifically to an analyte is immobilized; surface plasmon being generated by irradiating the metal microstructure with excitation light,
- an inlet through which a second VHH antibody and a sample that may contain an analyte are introduced, wherein the second VHH antibody has a property of binding specifically to the analyte and is labeled with a fluorescent substance;
- a light irradiation unit for irradiating the metal microstructure to which the second VHH antibody and the sample have been introduced with the excitation light; and a detection unit for detecting the analyte on the basis of fluorescence generated from the fluorescent substance by the irradiation of the excitation light.

According to this configuration, it is possible to use a VHH antibody as the immobilized antibody and the labeled antibody in the surface enhanced fluorescence method in which the fluorescence based on the analyte is enhanced and detected by the surface plasmon. The VHH antibody is a variable region of a heavy chain antibody present in camelids (llama, alpaca, etc.). In other words, the VHH antibody is a single domain antibody of natural origin and smaller than a normal IgG antibody. Furthermore, the VHH antibody has higher antigen capturing ability than a fragmented antibody provided by fragmenting an IgG antibody. Therefore, by using the VHH antibody as the immobilized antibody and the labeled antibody, the fluorescence enhancement effect is improved without the decrease in the antigen capturing ability, and it is possible to detect a low concentration of the analyte with high sensitivity.

In the detection device according to one aspect of the present disclosure, arithmetic mean roughness (Ra) of a surface of the metal microstructure may be 50% or less of a size of the second VHH antibody.

According to this configuration, the arithmetic mean roughness of the surface of the metal microstructure can be 50% or less of the size of the second VHH antibody. Therefore, half or more of a portion of the second VHH antibody attached to the surface of the metal microstructure can be exposed. As a result, when the surface of the metal microstructure is cleaned, the second VHH antibody (labeled antibody) attached to the surface of the metal microstructure can be removed relatively easily to decrease nonspecific adsorption.

The size of the VHH antibody is defined by length of the longest side of the smallest rectangular solid enclosing a three-dimensional structural model of the VHH antibody. The three-dimensional structural model of the VHH antibody is constructed based on a primary structure of an amino acid of the VHH antibody using publically known protein structure prediction techniques.

In the detection device according to one aspect of the present disclosure, the metal microstructure may include a plurality of protrusions disposed on a plane of a substrate, and a length of a gap between adjacent protrusions in the plurality of protrusions may be 100% to 200% as long as a size of a complex consisting of the first VHH antibody, the analyte, and the second VHH antibody.

According to this configuration, the length of the gap between the adjacent protrusions of the metal microstructure can be made 100% to 200% as long as the size of the complex consisting of the first VHH antibody, the analyte, and the second VHH antibody. This makes it possible to balance the capturing ability of the analyte and the fluorescence enhancement effect by the surface plasmon. To capture the complex of the first VHH antibody, the second VHH antibody, and the analyte in the gap between the projections, a gap of 100% or more of the size of the complex is required. From the viewpoint of enhancing the electric field, it is preferable that the gap is narrow. A gap of 200% or more of the size capable of capturing the complex on both of the adjacent protrusions is excessive from the viewpoint of the capturing ability. In other words, by setting the length of the gap between the protrusions to 100% to 200% as long as the size of the complex, it is possible to balance the capturing ability of the analyte and the fluorescence enhancing ability by the surface plasmon.

In the detection device according to one aspect of the present disclosure, a self-assembled monolayer including a linker molecule and a non-linker molecule may be formed on a surface of the metal microstructure, and the first VHH antibody may be immobilized on the metal microstructure via the linker molecule.

According to this configuration, the SAM including the linker molecule and the non-linker molecule is formed on the surface of the metal microstructure. Therefore, the first VHH antibody can be immobilized by the linker molecule, while the non-linker molecule prevents the second VHH antibody and the fluorescent substance from attaching to the SAM. In other words, it is possible to decrease the nonspecific adsorption, while the immobilized amount of the first VHH antibody is maintained.

In the detection device according to one aspect of the present disclosure, the linker molecule may have a thiol group at one end thereof and a carboxyl group at the other end thereof, and may include an alkyl chain having 10 or more carbon atoms and an ethylene glycol chain, and the non-linker molecule may have a thiol group at one end thereof and a hydroxyl group at the other end thereof, and may include an alkyl chain having 10 or more carbon atoms and an ethylene glycol chain.

According to this configuration, the SAM can include an alkyl chain having 10 or more carbon atoms. As a result, a dense SAM can be realized, and coexistence of improvement of the ability to immobilize the first VHH antibody and decrease in the nonspecific adsorption can be achieved. Furthermore, the SAM can include an ethylene glycol chain. This allows the carboxyl group located at the end of the linker molecule to provide mobility. As a result, the binding between the first VHH antibody bound to the carboxyl group and the analyte is improved, and the nonspecific adsorption of the second VHH antibody and the fluorescent substance can be decreased due to steric hindrance.

In the detection device according to one aspect of the present disclosure, the metal microstructure may have an absorption region in a wavelength range corresponding to a wavelength of the excitation light and a wavelength of the fluorescence when an absorption spectrum is measured, and a peak width of the absorption region may be 500 nm or less.

According to this configuration, the peak width of the absorption region can be made 500 nm or less. By thus making the peak width of the absorption region present in the wavelength range corresponding to the wavelength of excitation light and the wavelength of fluorescence smaller than that of the prior art, surface plasmon closer to a single mode can be generated. As a result, the fluorescence can be enhanced more effectively.

In the detection device according to one aspect of the present disclosure, the wavelength of the excitation light and the wavelength of the fluorescence may be 600 nm to 850 nm.

According to this configuration, the wavelength of 600 nm to 850 nm can be used as the wavelength of the excitation light and the wavelength of the fluorescence. As a result, autofluorescence of the VHH antibody can be suppressed to enhance detection sensitivity, and a semiconductor laser can be used as a light source.

Note that these inclusive or specific aspects can be realized by a system, a method, an integrated circuit, a computer program, or a recording medium such as a computer-readable CD-ROM and that these inclusive or specific aspects can be realized by any combination of a system, a method, an integrated circuit, a computer program and a recording medium.

Hereinafter, embodiments will be specifically described with reference to the drawings.

Note that the embodiments which will be described below are all inclusive or specific examples. Numerical values, shapes, materials, elements, arrangement positions and connection forms of elements, steps, order of steps, and the like shown in the following embodiments are merely examples, and are not intended to limit the scope of the claims. Among the elements in the following embodiments, elements not described in the independent claim indicating the highest concept are described as arbitrary elements.

Moreover, each drawing is not necessarily illustrated exactly. In the drawings, substantially the same elements are denoted by the same reference numerals, and redundant description will be omitted or simplified.

Moreover, in the following embodiment, a case where an analyte is a component constituting a virus floating in air will be described (hereinafter, such a component will be simply referred to as virus); however, the analyte is not limited to such a component in the present disclosure. The component constituting the virus is, for example, a protein or nucleic acid constituting the virus. The kind of virus does not have to be particularly limited, and may be anything generally classified as a virus. The analyte does not have to be a virus.

First Embodiment

[Overview of Detection System]

FIG. 1 is a schematic view of a detection system 10 according to the first embodiment. The detection system 10 is provided, for example, in a room where people enter and leave. As shown in FIG. 1, the detection system 10 comprises a collection device 100, a detection device 200, and a controller 300. Hereinafter, details of the collection device 100, the detection device 200, and the controller 300 will be described.

[Details of Collection Device]

The collection device 100 collects fine particles that may contain viruses in the air and mixes them with a collection liquid. As shown in FIG. 1, the collection device 100 comprises a suction unit 102, a collection liquid tank 104, a pump 106, a cyclone 108, an air inlet 110, a cleaning liquid tank 112, a pump 114, and a waste liquid tank 120 and a liquid flow path 122. Hereinafter, each element of the collection device 100 will be described.

The suction unit 102 sucks air from the air inlet 110. The fine particles that may contain viruses floating in the air are drawn into the cyclone 108 through the air inlet 110 together with the air.

The collection liquid tank 104 is a container for holding the collection liquid for collecting the virus in the air.

The pump 106 supplies the collection liquid contained in the collection liquid tank 104 to the cyclone 108.

The cyclone 108 is connected to the air inlet 110 and the collection liquid tank 104, and mixes the fine particles that may contain the viruses in the air sucked from the air inlet 110 by the suction unit 102 and the collection liquid supplied from the collection liquid tank 104 by the pump 106. The cyclone 108 is connected to the detection device 200 via the liquid flow path 122. The collection liquid in which the fine particles have been mixed (hereinafter, such a collection liquid is referred to as a sample) is discharged from the cyclone 108 to the detection device 200 through the liquid flow path 122.

The cleaning liquid tank 112 is a container for holding a cleaning liquid for cleaning the cyclone 108 and the liquid flow path 122. The cleaning liquid tank 112 is connected to the cyclone 108, and the cleaning liquid in the cleaning liquid tank 112 is supplied to the cyclone 108 by the pump 114.

The waste liquid tank 120 is a container for storing unnecessary liquid.

The liquid flow path 122 is a path for guiding the sample output from the cyclone 108 to the detection device 200.

[Details of Detection Device]

Next, the detection device 200 will be described with reference to FIGS. 1 and 2. FIG. 2 is a schematic view of the detection device 200 according to the first embodiment.

The detection device 200 detects a virus from the collection liquid in which the fine particles have been mixed by the collection device 100. As shown in FIGS. 1 and 2, the detection device 200 comprises a sensor device 202, an inlet 206, a light source 208, a beam splitter 210, a lens 212, and a detection unit 214. Hereinafter, each element of the detection device 200 will be described.

The sensor device 202 comprises a sensor cell 204. Note that, in FIG. 1, although the sensor device 202 is provided with the single sensor cell 204, the sensor device 202 may be provided with a plurality of sensor cells.

In the present embodiment, the sensor device 202 can detect a virus within a concentration range of 0.1 pM to 100 nM. In the present embodiment, a surface enhanced fluorescence method is used to optically detect the amount of the virus.

The sensor cell 204 enhances the fluorescence from the fluorescent substance bound to the virus by generating surface plasmon when the sensor cell 204 is irradiated with excitation light. As shown in FIG. 2, the sensor cell 204 comprises a flow path **204*a* and a detection region 204*b***.

The flow path **204*a* is a path for guiding, to the detection region 204*b*, a sample liquid 2061 dropped from the inlet 206**.

The detection region **204*b* is a region for optically detecting a virus using surface plasmon. A metal microstructure is disposed in the detection region 204*b*, and surface plasmon is generated by irradiating the detection region 204*b* with excitation light from the light source 208. The first VHH antibody is immobilized on the metal microstructure. The first VHH antibody is an immobilized antibody capable of binding specifically to the virus. Details of the detection region 204*b* will be described later with reference to FIGS. 3A and 3B**.

The inlet 206 introduces the second VHH antibody and the sample into the sensor cell 204. Specifically, the inlet 206 drops the sample liquid 2061 containing the second VHH antibody and the sample onto the sensor cell 204. The second VHH antibody is a labeled antibody labeled with a fluorescent substance. The sample is a liquid that may contain a virus, and, in the present embodiment, the sample is a collection liquid discharged from the cyclone 108.

If the sample contains a virus, the virus binds to the metal microstructure via the first VHH antibody. At this time, the virus is also bound to the second VHH antibody labeled with the fluorescent substance. In other words, a complex of the first VHH antibody, the virus, the second VHH antibody and the fluorescent substance is bound to the metal microstructure. When the metal microstructure in this state is irradiated with light, fluorescence is emitted from the fluorescent substance indirectly bound to the virus, and the fluorescence is enhanced by the surface plasmon. Hereinafter, the fluorescence enhanced by the surface plasmon is referred to as surface enhanced fluorescence.

The light source 208 is an example of a light irradiation unit for irradiating the sensor cell 204 with excitation light. As the light source 208, publically known techniques can be used without particular limitation. For example, a laser such as a semiconductor laser or a gas laser can be used as the light source 208. Note that it is preferable that the light source 208 emits excitation light having a wavelength (e.g., 400 nm to 2000 nm) which has a small interaction with the substance contained in the virus. Furthermore, it is preferable that the wavelength of the excitation light is a wavelength of 600 nm to 850 nm capable of being used by the semiconductor laser.

The beam splitter 210 separates the surface enhanced fluorescence generated in the detection region 204b from the excitation light emitted from the light source 208. Specifically, the beam splitter 210 passes the excitation light from the light source 208, separates the surface enhanced fluorescence generated in the sensor cell 204, and guides it to the detection unit 214.

The lens 212 collects the excitation light from the light source 208 which has passed through the beam splitter 210 in the detection region 204b.

The detection unit 214 splits the surface enhanced fluorescence guided by the beam splitter 210 and detects light in a specific wavelength band to output an electrical signal corresponding to the amount of the virus in the sample. The detection unit 214 can use a publically known technology such as a light receiving element capable of detecting light in a specific wavelength band without particular limitation. For example, as the detection unit 214, an interference filter capable of transmitting a specific wavelength band for separation of light, a Zellny spectroscope capable of splitting light using a diffraction lattice, an echelle spectroscope, or the like can be used. Furthermore, the detection unit 214 may include a notch filter for removing excitation light from the light source 208, or a long pass filter capable of blocking the excitation light from the light source 208 and passing the surface enhanced fluorescence generated in the sensor cell 204.

[Detail of Controller]

The controller 300 controls overall operation of the detection system 10. Specifically, the controller 300 controls the collection device 100 and the detection device 200.

More specifically, the controller 300 controls the start of the measurement to cause the suction unit 102 to start the suction of the surrounding air, and to cause the pump 106 to supply the collection liquid from the collection liquid tank 104 to the cyclone 108. As a result, the collection liquid and the fine particles are mixed in the cyclone 108, and the sample is supplied from the cyclone 108 to the detection device 200. Furthermore, the controller 300 causes the light source 208 to emit light and causes the detection unit 214 to detect the surface enhanced fluorescence.

For example, the controller 300 can control each pump on the basis of input parameters under preset conditions to supply a predetermined volume of the sample liquid 2061 to the detection device 200. Furthermore, the controller 300 has a clocking function, and may generate and store information on the time required for each operation. Further, the controller 300 may receive a measurement value from the detection device 200 and calculate temporal change of the concentration of the virus floating in the air on the basis of the measurement value and the time information.

Note that the controller 300 is realized by, for example, one or more dedicated electronic circuits. The one or more dedicated electronic circuits may be integrated on one chip or may be formed separately on a plurality of chips. The controller 300 may be realized by a general-purpose processor (not shown) and a memory (not shown) in which software programs or instructions have been stored, in place of the one or more dedicated electronic circuits. In this case, the processor functions as the controller 300 when the software program or the instruction is executed.

[Details of Detection Region of Sensor Cell]

Here, the detailed configuration of the detection region 204b of the sensor cell 204 will be specifically described with reference to FIGS. 3A and 3B.

Figure 3A:
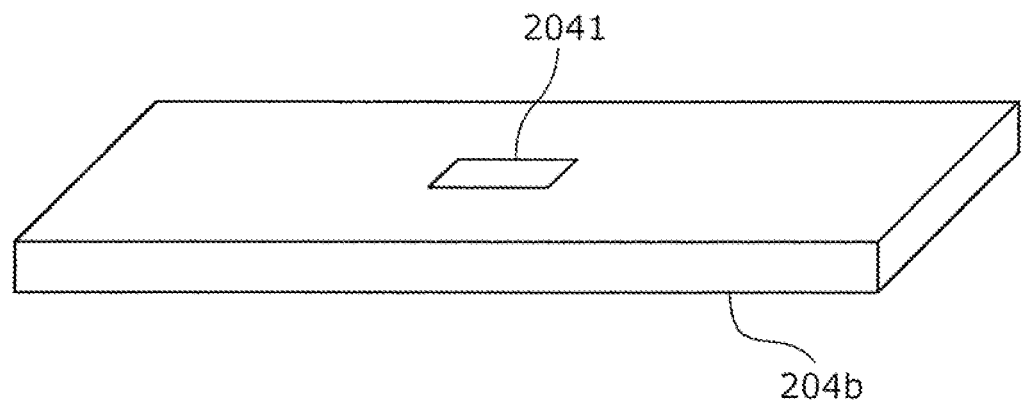
FIG. 3A is a perspective view of a detection region of a sensor cell in the first embodiment.
Figure 3B:
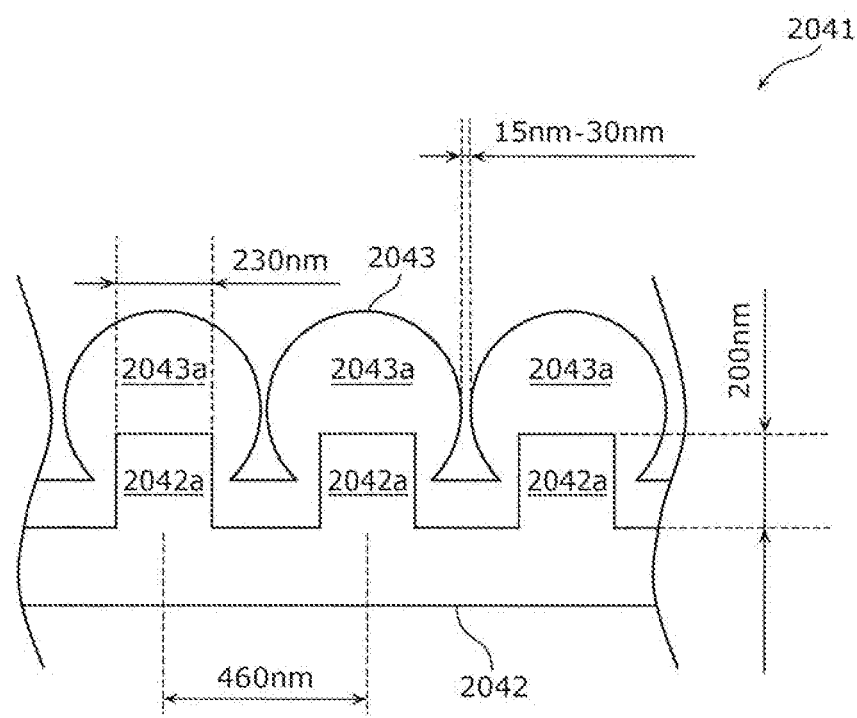
FIG. 3B is an enlarged cross-sectional view of a metal microstructure in the first embodiment.

FIG. 3A is a perspective view of the detection region 204b of the sensor cell 204 in the first embodiment. FIG. 3B is an enlarged cross-sectional view of a metal microstructure 2041 in the first embodiment.

As shown in FIG. 3A, a nanoscale metal microstructure 2041 for generating the surface plasmon is provided in the detection region 204b. In the present embodiment, as shown in FIG. 3B, the metal microstructure 2041 comprises a resin substrate 2042 and a metal film 2043.

The resin substrate 2042 has a nanostructure formed by nanoimprinting or injection molding. Here, the nanostructure includes a plurality of pillars 2042a. In the plurality of pillars 2042a, the ratio of the height of the pillars to the size of the pitch between the pillars is desirably 1:1 to 1:3. In the present embodiment, the wavelength of excitation light and the wavelength of fluorescence are 750 nm to 850 nm. Therefore, in the present embodiment, for example, it is desirable that the pillar height is about 200 nm, the pillar diameter is about 230 nm, and the inter-pillar pitch is about 460 nm. The nanostructure of the resin substrate 2042 is not limited to the above, and may include a plurality of hemispheres in place of the plurality of pillars.

The metal film 2043 is manufactured by forming a metal on the resin substrate 2042. A plurality of protrusions 2043a corresponding to the plurality of pillars 2042a of the resin substrate 2042 is formed with the metal film 2043. If the wavelength of the excitation light and the wavelength of the fluorescence are 750 nm to 850 nm, the thickness of the metal film 2043 is desirably about 400 nm. It is desirable that the length of the gap between adjacent protrusions in the plurality of protrusions 2043a is 100% to 200% as long as the size of the complex consisting of the first VHH antibody, the analyte, and the second VHH antibody (for example, 15 nm to 30 nm).

The material of the metal film 2043 is not particularly limited, and may be gold, silver, copper, aluminum, or an alloy containing any of these metals as a main component. In the present embodiment, electron beam (EB) evaporation is used as a method of forming the metal film 2043. The method for forming the metal film 2043 is not particularly limited, and may be, for example, sputtering or vacuum evaporation.

Figure 4:
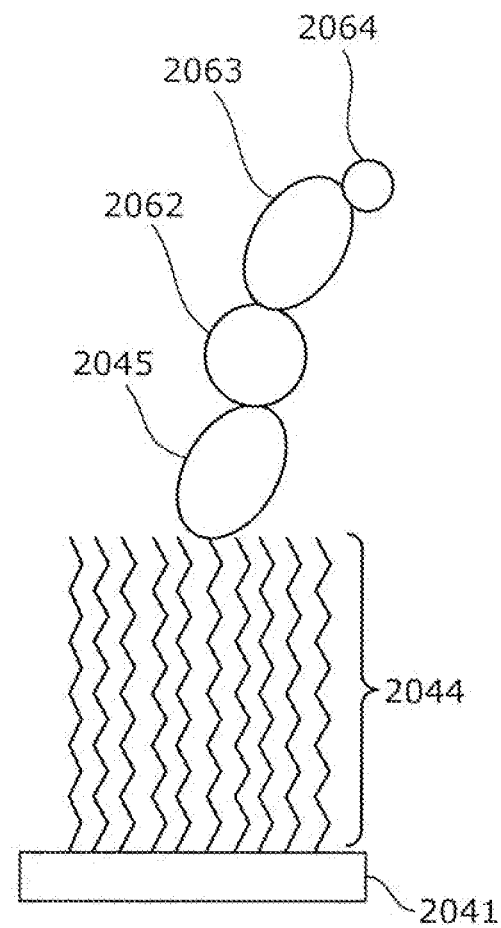
FIG. 4 is a diagram showing a SAM formed on the metal microstructure in the first embodiment.

A self-assembled monolayer (hereinafter, referred to as SAM) is formed on the metal film 2043, and the first VHH antibody is immobilized via this SAM on the metal microstructure 2041. FIG. 4 is a diagram showing a SAM 2044 on the metal microstructure 2041 in the first embodiment.

In FIG. 4, the SAM 2044 is formed on the metal microstructure 2041. In the present embodiment, the SAM 2044 includes an alkyl chain having, for example, about 6 carbon atoms. A first VHH antibody 2045 is immobilized on the metal microstructure 2041 via the SAM 2044.

If the sample liquid 2061 contains a virus (analyte) 2062, the virus 2062 binds to the first VHH antibody 2045 immobilized on the metal microstructure 2041. A second VHH antibody 2063 labeled with a fluorescent substance 2064 is also bound to the virus 2062.

When such a metal microstructure 2041 is irradiated with the excitation light, fluorescence is emitted from the fluorescent substance 2064, and the fluorescence is enhanced by the surface plasmon generated on the metal microstructure 2041. In other words, the surface enhanced fluorescence that corresponds to the amount of the virus is emitted.

[Operation of Detection Device]

Figure 5:
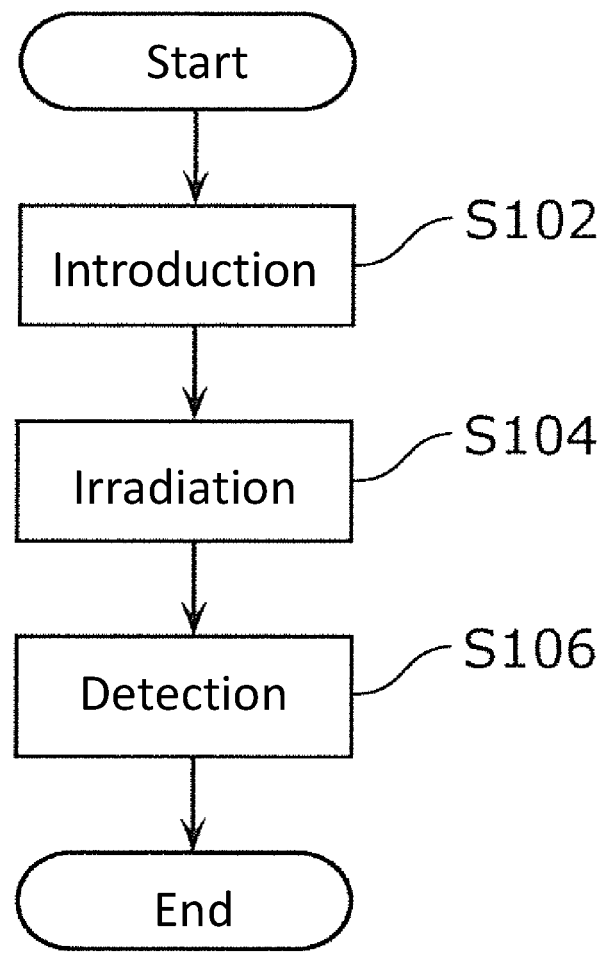
FIG. 5 is a flowchart showing operation of the detection device according to the first embodiment.

The operation of the detection device 200 configured as described above will be described with reference to FIG. 5. FIG. 5 is a flowchart showing the operation of the detection device 200 according to the first embodiment.

First, the inlet 206 introduces the sample liquid 2061 that may contain a virus into the metal microstructure 2041 (S102). Subsequently, the light source 208 emits excitation light to the metal microstructure 2041 into which the sample liquid 2061 has been introduced (S104). The detection unit 214 detects the virus in the sample liquid 2061 by measuring the fluorescence which has been generated from the fluorescent substance 2064 by the irradiation of the excitation light and which has been enhanced by the surface plasmon (S106).

Summary of First Embodiment

As described above, according to the detection device 200 according to the present embodiment, in the surface enhanced fluorescence method in which the fluorescence based on the analyte is enhanced and detected by the surface plasmon, the VHH antibody is allowed to be used as the immobilized antibody and the labeled antibody. The VHH antibody is smaller than normal IgG antibodies, and has higher antigen capturing ability than fragmented IgG antibodies. Therefore, by using a VHH antibody as the immobilized antibody and the labeled antibody, the virus is captured effectively and the fluorescence enhancement effect by the surface plasmon is improved. As a result, a low concentration of the analyte is allowed to be detected with high sensitivity.

According to the detection device 200 according to the present embodiment, the length of the gap between the adjacent protrusions 2043a of the metal microstructure 2041 can be made 100% to 200% as long as the size of the complex consisting of the first VHH antibody, the analyte, and the second VHH antibody. This makes it possible to balance the capturing ability of the analyte and the fluorescence enhancing ability by surface plasmon. To capture the complex of the first VHH antibody, the second VHH antibody, and the analyte in the gap between the projections, a gap of 100% or more of the size of the complex is required. From the viewpoint of enhancing the electric field, it is preferable that the gap is narrow. A gap of 200% or more of the size capable of capturing the complex on both of the adjacent protrusions is excessive from the viewpoint of capturing ability. In other words, by setting the length of the gap between the protrusions to 100% to 200% as long as the size of the complex, it is possible to balance the capturing ability of the analyte and the fluorescence enhancing ability by the surface plasmon.

Second Embodiment

Next, a second embodiment will be described. In the first embodiment, the detection sensitivity of the low concentration of the analyte is improved by using the VHH antibody as the immobilized antibody and the labeled antibody. However, if a VHH antibody is used, it is difficult to accurately measure an amount of a high concentration of an analyte. The present inventors have found that the reason therefor is nonspecific adsorption.

Nonspecific adsorption means that the second VHH antibody or the fluorescent substance is directly attached to the metal film, the SAM or the first VHH antibody without the analyte. If the nonspecific adsorption occurs, fluorescence will be emitted even if the analyte is absent. In other words, the nonspecific adsorption increases noise, decreases a S/N ratio, and decreases detection accuracy of the amount of the analyte.

The VHH antibody is smaller than conventional antibodies (e.g., IgG antibodies), and the nonspecific adsorption of the VHH antibody occur more often than the nonspecific adsorption of conventional antibodies. Therefore, if the VHH antibody is used in the surface enhanced fluorescence method, the detection accuracy of the high concentration of the analyte is decreased, compared to the conventional antibody. Therefore, to use the VHH antibody in the surface enhanced fluorescence method, a decrease in the nonspecific adsorption is required.

To solve the problem, in the present embodiment, to decrease the nonspecific adsorption, a metal microstructure having a smoother surface is used. Hereinafter, a detection system having such a metal microstructure will be described with reference to the drawings.

The configurations of the collection device and the controller according to the present embodiment are substantially the same as the configurations of the collection device and the controller according to the first embodiment. The configuration of the detection device according to the present embodiment is substantially the same as the configuration of the detection device according to the first embodiment, except for the metal microstructure of the sensor cell. Therefore, the detection system according to the present embodiment will be described, focusing on the metal microstructure, which is different from the first embodiment.

[Structure of Metal Microstructure]

Figure 6:
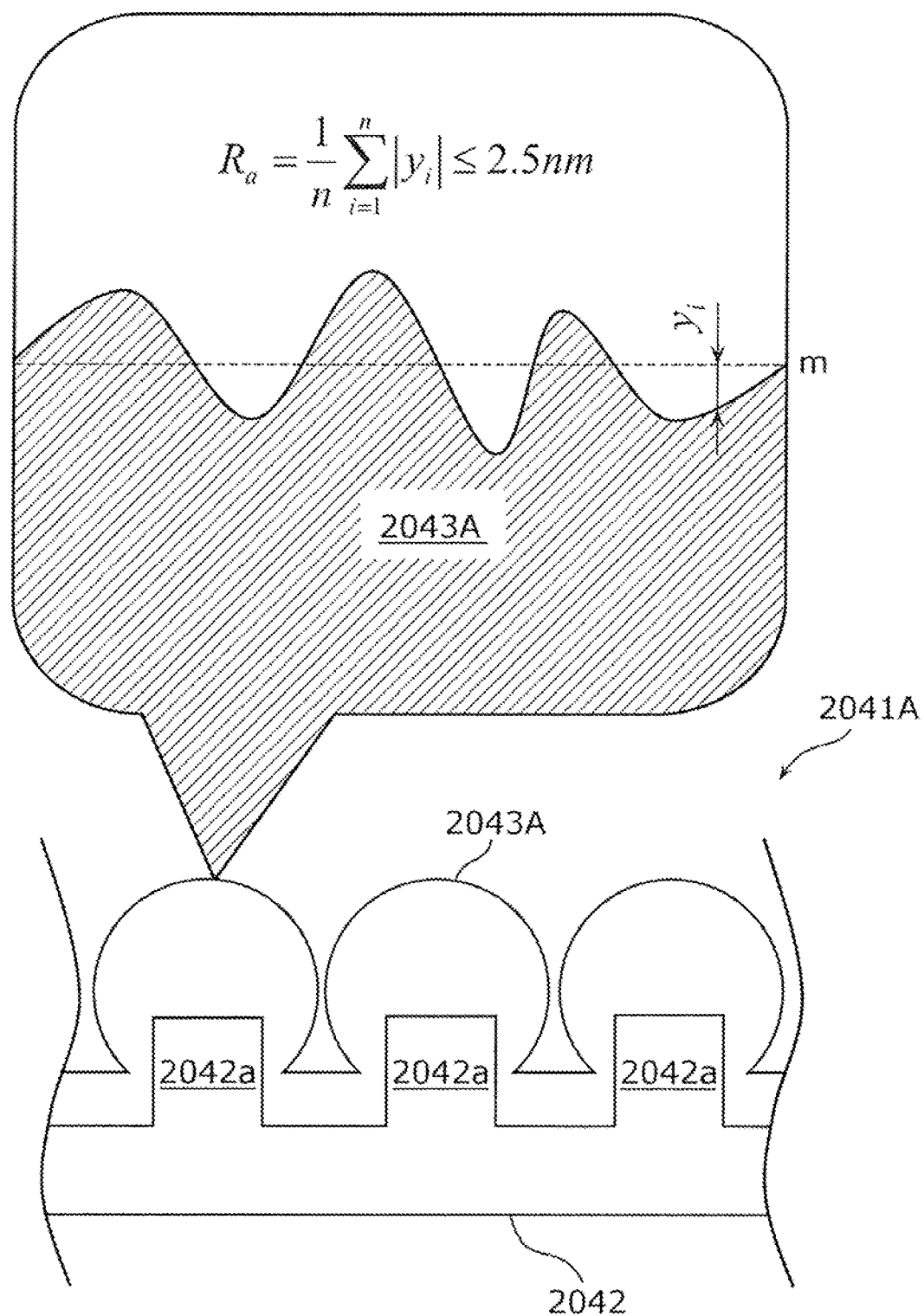
FIG. 6 is an enlarged cross-sectional view of the metal microstructure in a second embodiment.

FIG. 6 is an enlarged cross-sectional view of a metal microstructure 2041A in the second embodiment. The metal microstructure 2041A comprises the resin substrate 2042 and a metal film 2043A. In the present embodiment, the metal film 2043A is formed by depositing gold on the resin substrate 2042 by sputtering.

By forming a film of gold by sputtering in this manner, the arithmetic mean roughness (Ra) of the surface of the metal microstructure 2041A is allowed to be 2.5 nm or less. In other words, the arithmetic mean roughness (Ra) of the surface of the metal microstructure 2041A is allowed to be 50% or less of the size of the second VHH antibody (about 5 nm). If a gold film is formed by an EB evaporation, the arithmetic mean roughness of the surface of the metal microstructure is about 10 nm. The arithmetic mean roughness (Ra) is represented by the following equation (1).

[Mathematical formula 1]

$$R_a = \frac{1}{n}\sum_{i=1}^{n}|y_i| \quad (1)$$

where, n is the number of samples, and i is an ordinal number from 1 to n. yi is a vertical distance from the mean line m to the i-th sample point. The arithmetic mean roughness may be measured, for example, using an atomic force microscope (AFM); however, the measurement method is not particularly limited.

[Absorption Characteristic of Metal Microstructure]

Figure 7:
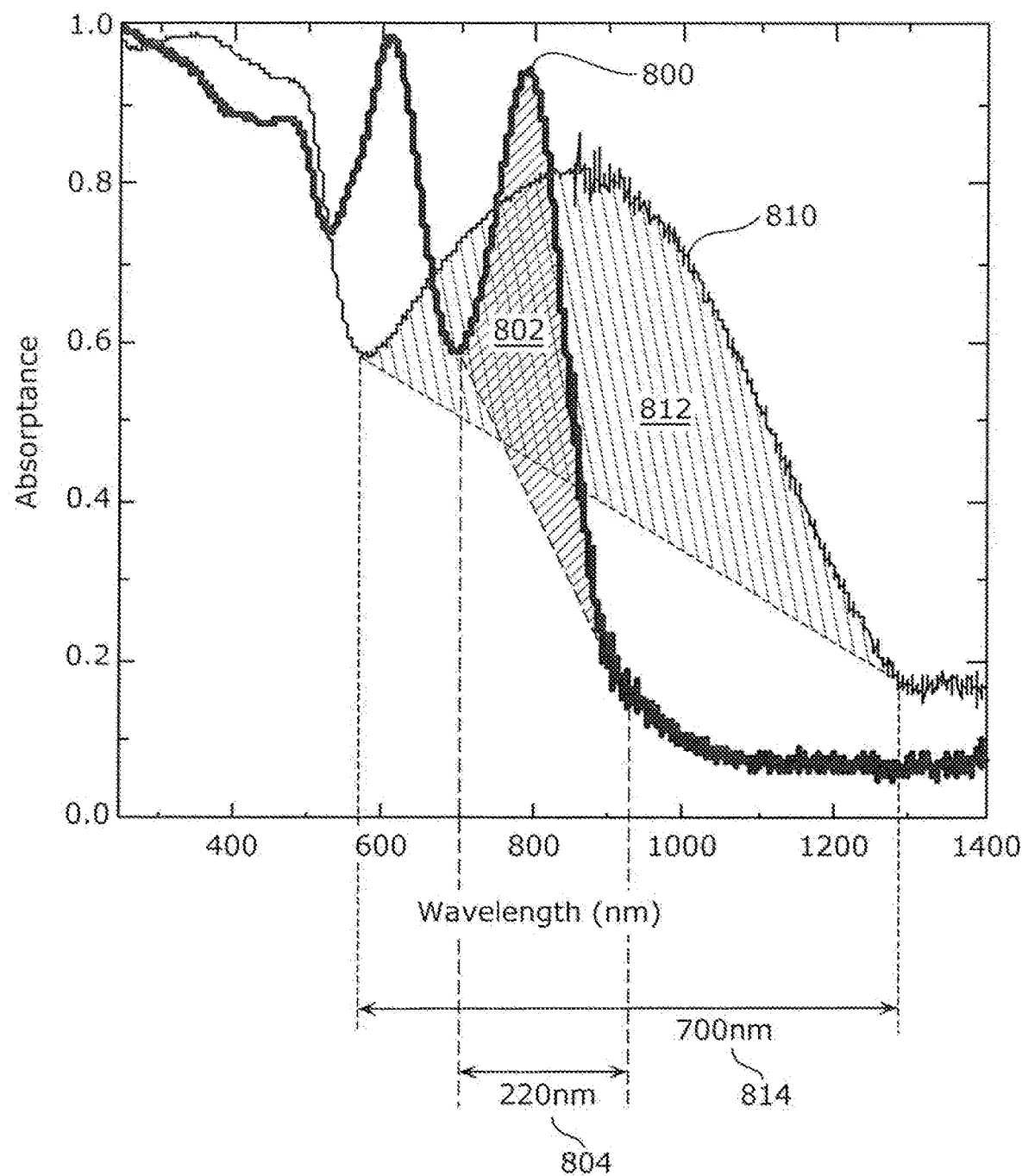
FIG. 7 is a graph showing an absorption characteristic of the metal microstructure in the second embodiment.

Next, the absorption characteristic of the metal microstructure 2041A according to the present embodiment will be described with reference to FIG. 7. FIG. 7 is a graph showing an absorption characteristic of the metal microstructure 2041A in the second embodiment.

In FIG. 7, the vertical axis represents an absorptance, and the horizontal axis represents a wavelength. An absorption spectrum 800 indicates the absorption characteristic of the metal microstructure 2041A having a gold film prepared by sputtering. An absorption spectrum 810 indicates the absorption characteristic of the metal microstructure 2041 having a gold film prepared by the EB evaporation.

In the present embodiment, each of the wavelength of excitation light and the wavelength of fluorescence is included in a wavelength band of 750 nm to 800 nm. Therefore, the metal microstructure 2041A having a metal film formed by sputtering has an absorption region 802 within a wavelength range corresponding to the wavelength of the excitation light and the wavelength of the fluorescence, when the absorption spectrum is measured. In other words, the absorption spectrum 800 of the metal microstructure 2041A has an absorption region 802 within the wavelength range including the wavelength of the excitation light and the wavelength of the fluorescence. At this time, a peak width 804 of the absorption region 802 is 500 nm or less, and specifically, 220 nm in FIG. 7.

The absorption spectrum 810 of the metal microstructure 2041 having a metal film formed by the EB evaporation has an absorption region 812 within a wavelength range corresponding to the wavelength of the excitation light and the wavelength of the fluorescence. A peak width 814 of the absorption region 812 is greater than 500 nm, specifically, 700 nm in FIG. 7.

The absorption region is a region defined on the basis of the maximum value of the absorption factor of the absorption spectrum and two minimum values on both sides of the maximum value. The peak width of the absorption region is determined by the difference value of the wavelengths of the two minimum values on both sides of the maximum value.

[Effect]

As described above, in the detection device 200 according to the present embodiment, the surface of the metal microstructure 2041A can be smoothed by depositing gold by sputtering. As a result, the nonspecific adsorption of the second VHH antibody 2063 and the fluorescent substance 2064 to the metal microstructure 2041A is allowed to be decreased.

Specifically, in the present embodiment, since the surface of the metal microstructure 2041A is smooth, even if the second VHH antibody 2063 and the fluorescent substance 2064 adhere to the surface, the second VHH antibody 2063 and the fluorescent substance 2064 are easily removed by cleaning. On the other hand, if a gold film is deposited by, for example, an EB evaporation, the surface of the metal microstructure is not relatively smooth and microscopically has gaps. If the second VHH antibody 2063 and the fluorescent substance 2064 enter the gap, it is difficult to remove the second VHH antibody 2063 and the fluorescent substance 2064 even if the surface of the metal microstructure is cleaned up.

In particular, in the detection device 200 according to the present embodiment, the arithmetic mean roughness of the surface of the metal microstructure 2041A can be 50% or less of the size of the second VHH antibody. Therefore, half or more of the portion of the second VHH antibody which has attached to the surface of the metal microstructure 2041A is allowed to be exposed. Therefore, when the surface of the metal microstructure 2041A is cleaned, the second VHH antibody 2063 (labeled antibody) which has attached to the surface of the metal microstructure 2041A can be removed relatively easily, and the decrease in the nonspecific adsorption is achieved.

In the present embodiment, since the surface of the metal microstructure 2041A is smooth, a more dense SAM 2044 can be formed. If the SAM 2044 is dense, a hydrophobic surface of the SAM 2044 can be enclosed in the SAM 2044. Since the nonspecific adsorption occurs due to hydrophobic interaction of SAM with the hydrophobic surface, the nonspecific adsorption can be suppressed by enclosing the hydrophobic surface of the SAM 2044 in the SAM 2044. On the other hand, if the surface of the metal microstructure is not smooth, the self-assembled single molecule is randomly oriented. Therefore, a dense SAM fails to be formed, the hydrophobic surface of the SAM is exposed to the outside, and it is difficult to suppress the nonspecific adsorption.

In the present embodiment, the absorption spectrum 800 including the absorption region 802 having a peak width 804 of 500 nm or less can be realized as the absorption spectrum of the metal microstructure 2041A. Therefore, the peak width of the absorption region present in the wavelength range corresponding to the wavelength of the excitation light and the wavelength of the fluorescence can be made smaller than that of the prior art, and the surface plasmon closer to the single mode is allowed to be generated. As a result, the fluorescence can be enhanced more effectively.

Third Embodiment

Next, the third embodiment will be described. In the present embodiment, the configuration of the SAM is different from that of the second embodiment. Hereinafter, the detection device according to the present embodiment will be described, focusing on differences from the second embodiment.

Note that the configurations of the collection device and the controller according to the present embodiment are substantially the same as those of the collection device and the controller according to the second embodiment. The configuration of the detection device according to the present embodiment is substantially the same as the configuration of the detection device according to the second embodiment, except for the SAM. Therefore, the detection system according to the present embodiment will be described, focusing on the SAM, which is different from the second embodiment.

[Configuration of SAM]

Figure 8:
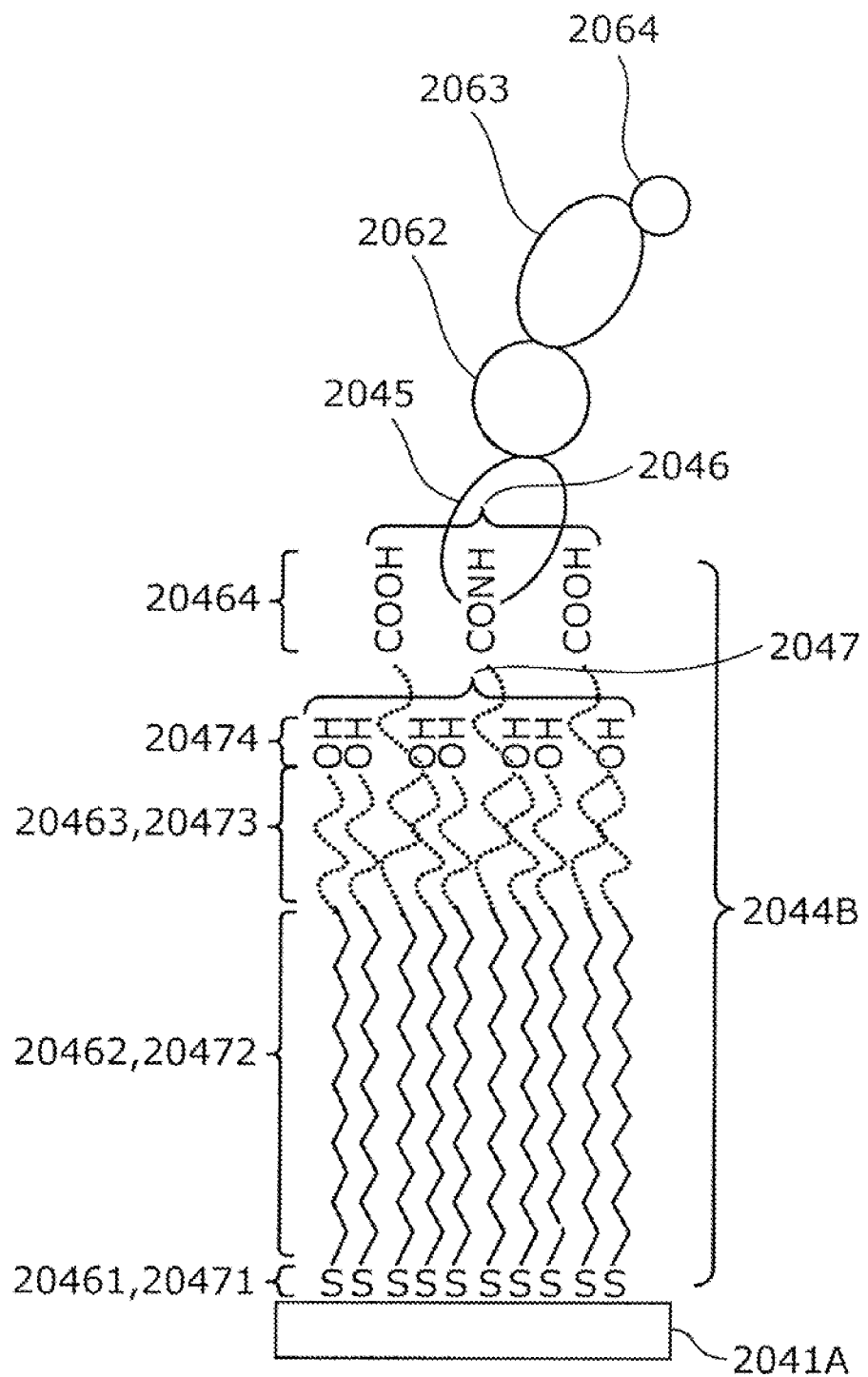
FIG. 8 is a diagram showing a SAM formed on a metal microstructure in a third embodiment.

FIG. 8 is a diagram showing a SAM 2044B on the metal microstructure 2041A in the third embodiment. As shown in FIG. 8, the SAM 2044B including a linker molecule 2046 and a non-linker molecule 2047 is formed on the surface of the metal microstructure 2041A. The first VHH antibody 2045 is immobilized on the metal microstructure 2041A via the linker molecule 2046.

The linker molecule 2046 has a thiol group 20461 at one end thereof and a carboxyl group 20464 at the other end thereof. The thiol group 20461 is bound to the surface of the metal microstructure 2041A. The carboxyl group 20464 is bound to the first VHH antibody 2045.

Furthermore, the linker molecule 2046 includes an alkyl chain 20462 having 10 or more carbon atoms and an ethylene glycol chain 20463 between the thiol group 20461 and the carboxyl group 20464. Specifically, the alkyl chain 20462 is connected to the thiol group 20461 and the ethylene glycol chain 20463, and the ethylene glycol chain 20463 is connected to the alkyl chain 20462 and the carboxyl group 20464.

The non-linker molecule 2047 has a thiol group 20471 at one end thereof and a hydroxyl group 20474 at the other end thereof. The thiol group 20471 is bound to the surface of the metal microstructure 2041A. Since the hydroxyl group 20474 is hydrophilic, the hydroxyl group 20474 prevents the nonspecific adsorption of the second VHH antibody 2063 and the fluorescent substance 2064.

Furthermore, the non-linker molecule 2047 includes an alkyl chain 20472 having 10 or more carbon atoms and an ethylene glycol chain 20473 between the thiol group 20471 and the hydroxyl group 20474. Specifically, the alkyl chain 20472 is connected to the thiol group 20471 and the ethylene glycol chain 20473, and ethylene glycol chain 20473 is connected to the alkyl chain 20472 and the hydroxyl group 20474.

In the present embodiment, the number of linker molecules 2046 contained in the SAM 2044B is smaller than that of the non-linker molecule 2047.

[Effects]

As described above, according to the detection device 200 according to the present embodiment, the SAM 2044B including the linker molecule 2046 and the non-linker molecule 2047 is formed on the surface of the metal microstructure 2041A. Therefore, the first VHH antibody 2045 can be immobilized by the linker molecule 2046, while the second VHH antibody 2063 and the fluorescent substance 2064 are prevented by the non-linker molecule 2047 from attaching to the SAM 2044B. In other words, the nonspecific adsorption can be decreased, while the ability to immobilize the first VHH antibody is maintained.

According to the detection device 200 according to the present embodiment, the SAM 2044B can include the alkyl chains 20462 and 20472 each having 10 or more carbon atoms. As a result, a dense SAM 2044B can be realized, and coexistence of the improvement of the ability to immobilize the first VHH antibody 2045 and the decrease in the non-specific adsorption can be achieved.

For example, in the first embodiment, the SAM 2044 including an alkyl chain having about 5 carbon atoms is used. By shortening the alkyl chain, the fluorescent substance 2064 approaches the surface of the metal microstructure 2041, so that the fluorescence enhancement effect by plasmon resonance is improved. On the other hand, in order to decrease the nonspecific adsorption, the alkyl chain is made longer in the present embodiment than in the first embodiment. In this way, by making the alkyl chain longer, the intermolecular force between adjacent alkyl chains can be increased to form a more dense SAM. As a result, a hydrophobic surface of the SAM, which is a site for the nonspecific adsorption, is firmly enclosed in the SAM, and the nonspecific adsorption can be decreased. Furthermore, since the dense SAM increases the number of the sites to which the immobilized antibodies binds, the number of the viruses each binding to the immobilized antibody also increases to increase a signal intensity. As mentioned above, the signal increases and the noise decreases, so that the detection sensitivity of the virus is improved.

In the present embodiment, there is a disadvantage that the distance between the fluorescent substance and the surface of the metal microstructure is increased due to the lengthening of the alkyl chain. However, the increase in the length of the alkyl chain in a case where one carbon is increased is approximately 0.15 nm. In other words, even if the number of carbons is increased by five, the increase in the length of the alkyl chain is about 0.75 nm, so that the disadvantage due to the increase in the distance between the fluorescent substance and the surface of the metal microstructure is relatively small.

According to the detection device 200 according to the present embodiment, the SAM 2044B can include the ethylene glycol chains 20463 and 20473. This allows the carboxyl group 20464 located at the end of the linker molecule 2046 to provide mobility. As a result, the binding between the first VHH antibody 2045 bound to the carboxyl group 20464 and the analyte is improved.

Specifically, the ethylene glycol chains 20463 and 20473 provides the carboxyl group 20464 located at the end of the linker molecule 2046 and the hydroxyl group 20474 located at the end of the non-linker molecule 2047 with the mobility. The binding of the first VHH antibody 2045 to the carboxyl group 20464 connected to the ethylene glycol chain 20463 of the linker molecule 2046 improves the binding between the first VHH antibody 2045 and the virus 2062.

If the ethylene glycol chain is absent, the mobility of the first VHH antibody immobilized on SAM is decreased. This increases possibility that a binding site to the virus 2062 in the first VHH antibody 2045 is not exposed, and that the virus 2062 and the first VHH antibody 2045 fail to bind to each other.

According to the detection device 200 according to the present embodiment, in the SAM 2044B, the number of the linker molecules 2046 is smaller than that of the non-linker molecule 2047. Thereby, the first VHH antibody 2045 can be appropriately immobilized, while the nonspecific adsorption is decreased, so that the detection accuracy is improved. The carboxyl group 20464 located at the end of the linker molecule 2046 binds to the first VHH antibody 2045. On the other hand, the hydroxyl group 20474 located at the end of the non-linker molecule 2047 is hydrophilic, so that the hydroxyl group 20474 suppresses the nonspecific adsorption of the second VHH antibody 2063 and the fluorescent substance 2064. As a result of experimenting with respect to a mixing ratio of the linker molecule 2046 and the non-linker molecule 2047, it has been found that, by increasing the proportion of the non-linker molecule 2047 compared to the linker molecule 2046, the first VHH antibody 2045 can be appropriately immobilized, and that the detection accuracy of the virus is improved, while the nonspecific adsorption is suppressed. The reason why the signal does not decrease significantly as compared to a case where the linker molecule 2046 is 100% is that the first VHH antibody has a size, so even if many carboxyl groups exist closely, the first VHH antibodies are not immobilized on all the carboxyl groups.

EXAMPLES

Hereinafter, the present disclosure will be described more specifically using the examples; however, these examples do not limit the present disclosure.

Inventive Example 1

In the present example, a resin substrate in which a nanostructure having a plurality of pillars was formed by nanoimprinting was used as a resin substrate of a metal microstructure. The pillar height was 200 nm, the pillar diameter was 230 nm, and the pillar pitch was 460 nm. A gold film was deposited so as to have a thickness of 400 nm on the resin substrate by sputtering to produce the metal microstructure. The metal microstructure was irradiated with excitation light having a wavelength of 785 nm by using a light source to emit fluorescence having a wavelength of 800 nm from a fluorescent substance. In the metal microstructure, a sharp plasmon resonance absorption peak was observed in the wavelength band of 650 nm to 850 nm.

A SAM was formed on the metal microstructure by immersing the metal microstructure in an SAM solution overnight at 40 degrees Celsius in an incubator.

The SAM solution was prepared by the following procedure. First, each of Carboxy-EG6-undecanethiol and Hydroxy-EG3-undecanethiol was diluted with ethanol and mixed with each other. Thereafter, a SAM solution was prepared by diluting with ethanol.

As the first VHH antibody and the second VHH antibody, alpaca-derived VHH antibodies each capable of binding specifically to an influenza virus nucleoprotein was prepared.

Thereafter, a peptide bond was formed by an EDC-NHS reaction between the carboxyl group located at the end of the SAM and the amino group located at the end of the first VHH antibody to immobilize the first VHH antibody on the SAM.

Here, the nucleoprotein (NP) of the influenza virus, which was the analyte, was bound to the first VHH antibody, and the second VHH antibody labeled with an organic fluorescent dye (emission wavelength 800 nm), which was the fluorescent substance, was bound to the NP to perform a sandwich assay.

An organic fluorescent dye was excited by irradiating, with a laser beam having a wavelength of 785 nm, the sample in which the sandwich assay had been performed, and an intensity of the fluorescence having a wavelength of 800 nm emitted from the organic fluorescent dye was measured.

Inventive Example 2

In the inventive example 2, the same manner as in the inventive example 1 was conducted, except that electron beam evaporation was used in place of sputtering as the method of forming the gold film.

Inventive Example 3

In the inventive example 3, the same manner as in the inventive example 1 was conducted, except that a solution containing Carboxy-hexanethiol was used as the SAM solution in place of the solution containing Carboxy-EG6-undecanethiol and Hydroxy-EG3-undecanethiol.

Inventive Example 4

In the inventive example 4, the same manner as in the inventive example 1 was conducted, except that electron beam evaporation was used in place of sputtering as the method of forming the gold film and that the solution containing Carboxy-hexanethiol was used as the SAM solution in place of the solution containing Carboxy-EG6-undecanethiol and Hydroxy-EG3-undecanethiol.

Comparative Example

In the comparative example, the same manner as in the inventive example 4 was conducted, except for the IgG antibody was used in place of the first VHH antibody and the second VHH antibody.

(Peak Intensity of Surface Enhanced Fluorescence for Low Concentration of NP)

The detection values of the peak intensity of the surface enhanced fluorescence for the low concentration (100 pM) of NP are shown in Table 1 for the inventive example 4 and the comparative example. As shown in Table 1, the peak intensity of the surface enhanced fluorescence for the low concentrations of NP is higher in the inventive example 4 than in the comparative example. In other words, the detection device of the inventive example 4 detected the low concentration of NP with higher sensitivity than the detection device of the comparative example, which used the IgG antibody.

TABLE 1

|  | NP 100 pM |
| --- | --- |
| Inventive example 4 | 2603 |
| Comparative example | 82 |

With regard to the inventive examples 1 to 3, the detection values of the peak intensity of the surface enhanced fluorescence with regard to the sample liquids in which the concentration of NP was 0 M (hereinafter, referred to as NP-0M) and the sample liquids in which the concentration of NP was 10 nM (hereinafter, referred to as NP-10 nM) and a S/N ratio (namely, a result dividing the PL intensity of NP-10 nM by the PL intensity of NP-0M) are shown in Table 2.

TABLE 2

|  | NP 0 M | NP 10 nM | S/N (=10 nM/0 M) |
| --- | --- | --- | --- |
| Inventive example 1 | 82 | 9644 | 118 |
| Inventive example 2 | 30 | 2347 | 78 |
| Inventive example 3 | 317 | 4911 | 15 |

In the NP-10 nM, the PL intensity of the inventive example 1 (9644) is about four times as large as the PL intensity of the inventive example 2 (2347). In sputtering, since the surface of the metal microstructure is smooth, a more uniform metal nanostructure is formed and plasmon resonance close to the single mode is generated. Therefore, the emission enhancement by the plasmon resonance is increased, and the PL intensity is increased. In the NP-0M, the PL intensity of the inventive example 1 (82) is larger than the PL intensity of the inventive example 2 (30). This is because the emission enhancement by the plasmon resonance is increased, and the nonspecific adsorption is not necessarily increased. In the NP-10 nM, from the comparison between the PL intensity of the inventive example 1 (9644) and the PL intensity of the inventive example 2 (2347), the enhancement by the surface plasmon in the inventive example 1 is estimated to be about four times as large as that of the inventive example 2. On the other hand, in the NP-0M, the PL intensity of the inventive example 1 (82) is about 3 times as large as the PL intensity of the inventive example 2 (30), so that the nonspecific adsorption is decreased more in the inventive example 1 than in the inventive example 2. From the above, the S/N ratio in the inventive example 1 (sputtering) is improved compared to the S/N ratio of the inventive example 2 (EB evaporation), and the detection is allowed to be conducted with higher sensitivity in the inventive example 1 than in the inventive example 2.

The SAM according to the inventive example 1 is a SAM having the linker molecule 2046 and the non-linker molecule 2047 in the third embodiment. The SAM according to the inventive example 3 is a SAM including an alkyl chain having about 6 carbon atoms in the first and second embodiments. In the NP-0M, the PL intensity of the inventive example 1 (82) is decreased to about ⅓ of the PL intensity of the inventive example 3 (317). This reveals that the nonspecific adsorption is decreased. On the other hand, in the NP-10 nM, the PL intensity of the inventive example 1 (9644) is increased to about 1.4 times of the PL intensity of the inventive example 3 (4911). As a result, the S/N ratio of the inventive example 1 increases to about 5 times of the S/N ratio of the inventive example 3, and the detection is allowed to be conducted with higher sensitivity in the inventive example 1 than in the inventive example 3.

As described above, in the inventive example 1, by using the metal microstructure having the smooth surface and the SAM having the linker molecule 2046 including an alkyl chain having 10 or more carbon atoms and the non-linker molecule 2047, the virus was allowed to be detected with higher sensitivity than in the inventive examples 2 and 3.

Other Embodiments

In each of the above embodiments, the sensor cell is formed of the resin substrate and the metal film; however, the sensor cell is not limited to such a sensor cell. For example, in the sensor cell, the metal microstructure may be produced by photolithography using a glass substrate, or the metal microstructure may be produced by Au film over nanosphere (AuFON).

In each of the above embodiments, the SAM is formed on the metal microstructure; however, the SAM does not have to be formed. In other words, the SAM does not have to be formed on the metal film.

In each of the above embodiments, the detection device 200 detects the surface enhanced fluorescence using the beam splitter 210 and the lens 212; however, the detection device 200 is not limited to this configuration.

In FIG. 7 of the second embodiment, although the example in which both the wavelength of the excitation light and the wavelength of the fluorescence are included in one absorption region has been described, the wavelength of the excitation light and the wavelength of the fluorescence may be included individually in two absorption regions. Even in this case, surface plasmon can be generated efficiently and fluorescence can be effectively enhanced.

INDUSTRIAL APPLICABILITY

The detection device according to the present disclosure can be used for a detection system for detecting a concentration of floating virus in the air of a room with high sensitivity in order to decrease the risk of infection of the virus to people staying in the room.

REFERENTIAL SIGNS LIST

10 Detection system
100 Collection device
102 Suction unit
104 Collection liquid tank
106, 114 Pump
108 Cyclone
110 Air inlet
112 Cleaning liquid tank
120 Waste liquid tank
122 Liquid channel
200 Detection device
202 Sensor device
204 Sensor cell
204a Flow path
204b Detection region
206 Inlet
208 Light source
210 Beam splitter
212 Lens
214 Detection unit
2041, 2041A Metal microstructure
2042 Resin substrate
2042a Pillar
2043, 2043A Metal film
2043a Protrusions
2044, 2044B SAM
2045 First VHH antibody
2046 Linker molecule
2047 Non-linker molecule
2061 Sample liquid
2062 Virus (Analyte)
2063 Second VHH antibody
2064 Fluorescent substance
20461, 20471 Thiol group
20462, 20472 Alkyl chain
20463, 20473 Ethylene glycol chain
20464 Carboxyl group
20474 Hydroxyl group

The invention claimed is:

1. A detection device, comprising:
a metal microstructure on which a first VHH antibody having a property of binding specifically to an analyte is immobilized; surface plasmon being generated by irradiating the metal microstructure with excitation light,
an inlet through which a second VHH antibody and a sample that may contain an analyte are introduced, wherein the second VHH antibody has a property of binding specifically to the analyte and is labeled with a fluorescent substance;
a light irradiation unit for irradiating the metal microstructure to which the second VHH antibody and the sample have been introduced with the excitation light; and
a detection unit for detecting the analyte on the basis of fluorescence generated from the fluorescent substance by the irradiation of the excitation light,
wherein an arithmetic mean roughness (Ra) of a surface of the metal microstructure is at most 50% of a size of the second VHH antibody.

2. The detection device according to claim 1, wherein the metal microstructure includes a plurality of protrusions disposed on a plane of a substrate; and
a length of a gap between adjacent protrusions in the plurality of protrusions is 100% to 200% as long as a size of a complex consisting of the first VHH antibody, the analyte, and the second VHH antibody.

3. The detection device according to claim 1, wherein a self-assembled monolayer including a linker molecule and a non-linker molecule is formed on a surface of the metal microstructure; and
the first VHH antibody is immobilized on the metal microstructure via the linker molecule.

4. The detection device according to claim 3, wherein the linker molecule has a thiol group at one end thereof and a carboxyl group at the other end thereof, and includes an alkyl chain having 10 or more carbon atoms and an ethylene glycol chain, and
the non-linker molecule has a thiol group at one end thereof and a hydroxyl group at the other end thereof, and includes an alkyl chain having 10 or more carbon atoms and an ethylene glycol chain.

5. The detection device according to claim 1, wherein the metal microstructure has an absorption region in a wavelength range corresponding to a wavelength of the excitation light and a wavelength of the fluorescence when an absorption spectrum is measured, and a peak width of the absorption region is not more than 500 nm.

6. The detection device according to claim 1, wherein the wavelength of the excitation light and the wavelength of the fluorescence are 600 nm to 850 nm.

7. A detection method, comprising:
an introduction step of introducing a sample and a second VHH antibody into a metal microstructure;
wherein:
   the sample may contain an analyte;
   the second VHH antibody has a property of binding specifically to the analyte and labeled with a fluorescent substance;
   a first VHH antibody having a property of binding specifically to the analyte is immobilized on the metal microstructure; and
   an arithmetic mean roughness (Ra) of a surface of the metal microstructure is at most 50% of a size of the second VHH antibody;
an irradiation step of irradiating the metal microstructure to which the second VHH antibody and the sample have been introduced with the excitation light to generate surface plasmon on the metal microstructure; and
a detection step of detecting the analyte on the basis of fluorescence generated from the fluorescent substance by the irradiation of the excitation light.

8. The detection device according to claim 1, wherein the arithmetic mean roughness (Ra) is 2.5 nm or less.

9. The detection method according to claim 7, wherein the arithmetic mean roughness (Ra) is 2.5 nm or less.

* * * * *